US00PP35964P2

(12) United States Plant Patent
Barnes

(10) Patent No.: US PP35,964 P2
(45) Date of Patent: Jul. 2, 2024

(54) ***SALVIA* PLANT NAMED 'WNSVRDP23'**

(50) Latin Name: *Salvia hybrida*
Varietal Denomination: WNSVRDP23

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/129,059

(22) Filed: Mar. 30, 2023

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Salvia* plant named 'WNSVRDP23', characterized by its relatively compact, upright to somewhat outwardly spreading plant habit; vigorous growth habit and rapid growth rate; freely branching habit; dense and bushy plant form; strong and sturdy lateral branches; dark green-colored leaves; early and freely flowering habit; upright inflorescences with deep dark purple-colored flowers and darker-colored calyces; and excellent container and garden performance.

2 Drawing Sheets

Figure 1:
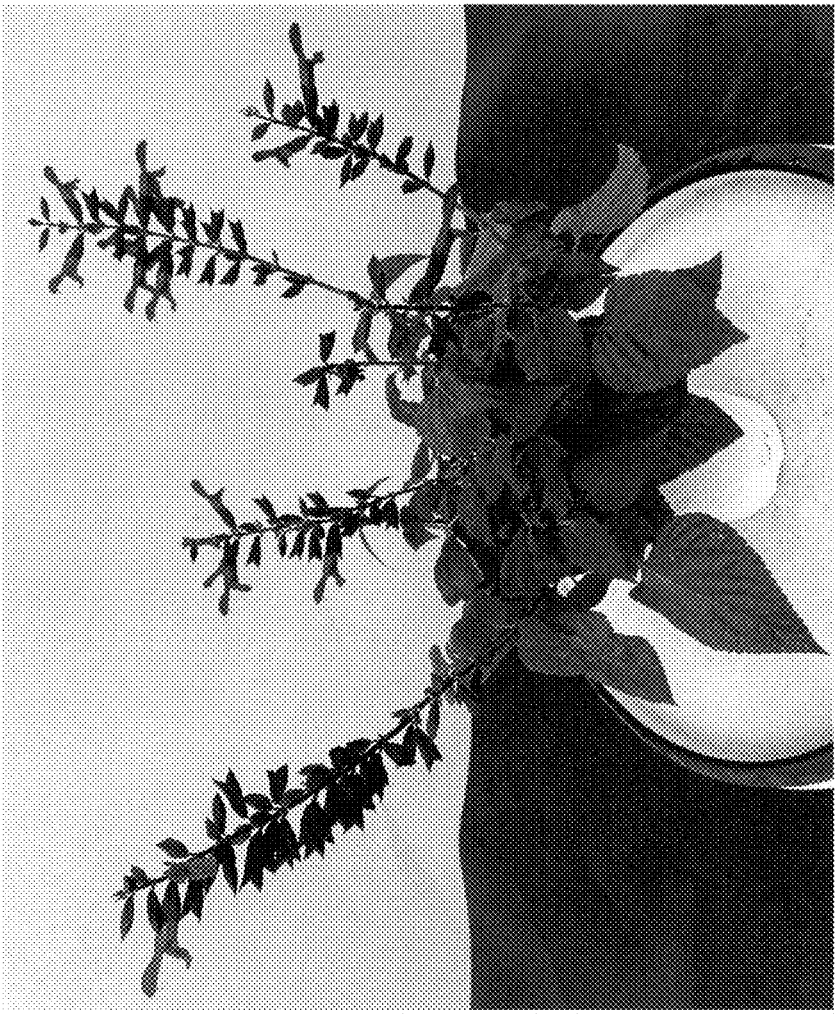

Botanical designation: *Salvia hybrida.*
Cultivar denomination: 'WNSVRDP23'.

BACKGROUND OF THE INVENTION

The present invention relates to a new and distinct cultivar of *Salvia* plant, botanically known as *Salvia hybrida* and hereinafter referred to by the name 'WNSVRDP23'.

The new *Salvia* plant is a product of a planned breeding program conducted by the Inventor in Bonsall, California. The objective of the breeding program is to create new compact and uniform *Salvia* plants with attractive leaves and flowers and good garden performance.

The new *Salvia* plant originated from a cross-pollination made by the Inventor on Aug. 24, 2018 of a proprietary selection of *Salvia hybrida* identified as code number 16SB116-04, not patented, as the female, or seed, parent with a proprietary selection of *Salvia hybrida* identified as code number 17SB159-03, not patented, as the male, or pollen, parent. The new *Salvia* plant was discovered and selected by the Inventor as a single flowering plant from within the progeny of the stated cross-pollination in a controlled greenhouse environment in Bonsall, California on Aug. 12, 2019.

Asexual reproduction of the new *Salvia* plant by vegetative terminal cuttings in Bonsall, California, since Aug. 22, 2019 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNSVRDP23'. These characteristics in combination distinguish 'WNSVRDP23' as a new and distinct *Salvia* plant:

1. Relatively compact, upright to somewhat outwardly spreading plant habit.
2. Vigorous growth habit and rapid growth rate.
3. Freely branching habit; dense and bushy plant form.
4. Strong and sturdy lateral branches.
5. Dark green-colored leaves.
6. Early and freely flowering habit.
7. Upright inflorescences with deep dark purple-colored flowers and darker-colored calyces.
8. Excellent container and garden performance.

Plants of the new *Salvia* can be compared to plants of the female parent selection. Plants of the new *Salvia* differ primarily from plants of the female parent selection in the following characteristics:

1. Plants of the new *Salvia* are shorter than plants of the female parent selection.
2. Plants of the new *Salvia* are more freely branching and denser than plants of the female parent selection.
3. Plants of the new *Salvia* have stronger and sturdier lateral branches than plants of the female parent selection.
4. Plants of the new *Salvia* are more tolerant to full sunlight conditions than plants of the female parent selection.

Plants of the new *Salvia* can be compared to plants of the male parent selection. Plants of the new *Salvia* differ primarily from plants of the male parent selection in the following characteristics:

1. Plants of the new *Salvia* are shorter than plants of the male parent selection.
2. Plants of the new *Salvia* are more tolerant to full sunlight conditions than plants of the male parent selection.

Plants of the new *Salvia* can be compared to plants of *Salvia hybrida* 'Amistad', disclosed in U.S. Plant Pat. No. 23,578. In side-by-side comparisons, plants of the new *Salvia* differ from plants of 'Amistad' in the following characteristics:

1. Plants of the new *Salvia* are shorter and more upright than plants of 'Amistad'.
2. Plants of the new *Salvia* are more freely branching and denser than plants of 'Amistad'.
3. Plants of the new *Salvia* have stronger and sturdier lateral branches than plants of 'Amistad'.
4. Leaves of plants of the new *Salvia* are broader and darker green in color than leaves of plants of 'Amistad'.

Plants of the new *Salvia* can also be compared to plants of *Salvia guaranitica* 'Black and Blue', not patented. In side-by-side comparisons, plants of the new *Salvia* differ from plants of 'Black and Blue' in the following characteristics:

1. Plants of the new *Salvia* are more compact than plants of 'Black and Blue'.
2. Plants of the new *Salvia* are denser than and not as open as plants of 'Black and Blue'.
3. Plants of the new *Salvia* have stronger and sturdier lateral branches than plants of 'Black and Blue'.
4. Plants of the new *Salvia* flower earlier than plants of 'Black and Blue'.
5. Flowers of plants of the new *Salvia* are deep dark purple in color whereas flowers of plants of 'Black and Blue' are blue in color.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

The photograph on the first sheet (FIG. 1) is a side perspective view of a typical flowering plant of 'WNSVRDP23' grown in a container.

Figure 2:
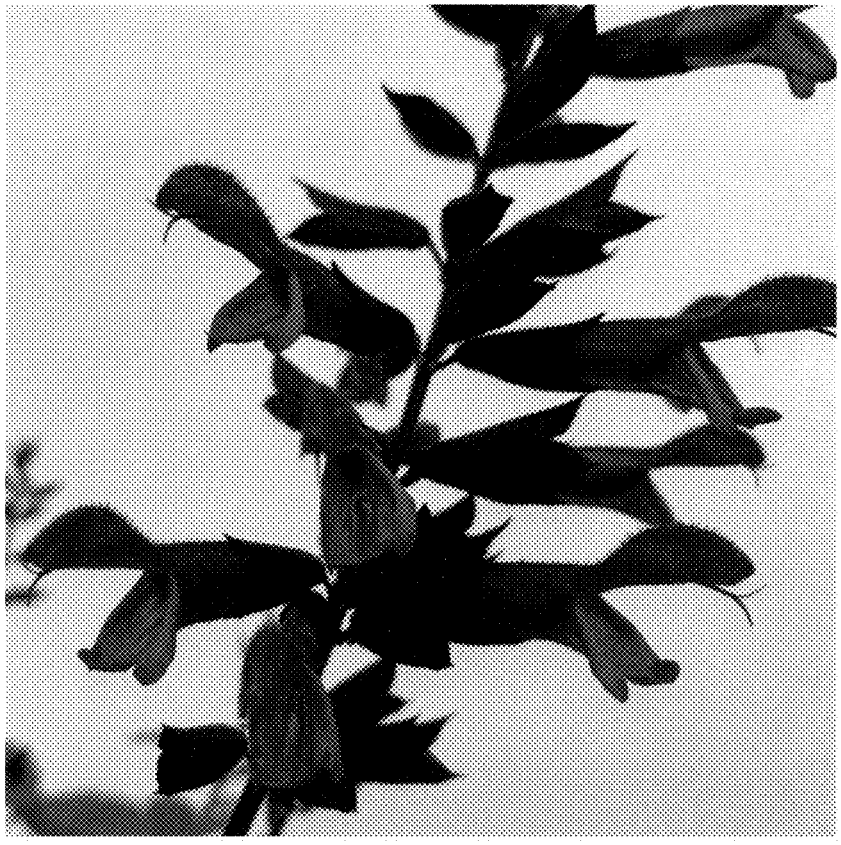

The photograph on the second sheet (FIG. 2) is a close-up view of a typical inflorescence of 'WNSVRDP23'.

DETAILED BOTANICAL DESCRIPTION

The aforementioned photographs and following observations and measurements describe plants grown during the summer in 740-ml containers in an acrylic-covered greenhouse in Carlton, Michigan and under cultural practices typical of commercial *Salvia* production. During the production of the plants, day temperatures ranged from 18 C to 32 C and night temperatures ranged from 18 C to 24 C. Plants were pinched one time seven weeks after planting rooted young plants; and plants were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Salvia hybrida* 'WNSVRDP23'.

Parentage:

*Female, or seed, parent.*—Proprietary selection of *Salvia hybrida* identified as code number 16SB116-04, not patented.

*Male, or pollen, parent.*—Proprietary selection of *Salvia hybrida* identified as code number 17SB159-03, not patented.

Propagation:

*Type.*—By vegetative terminal cuttings.

*Time to initiate roots, summer.*—About three days at ambient temperatures ranging from about 17 C to 29 C.

*Time to initiate roots, winter.*—About five days at ambient temperatures ranging from about 17 C to 21 C.

*Time to produce a rooted young plant from unrooted cuttings, summer.*—About 14 days at ambient temperatures ranging from about 17 C to 29 C.

*Time to produce a rooted young plant from unrooted cuttings, winter.*—About 17 days at ambient temperatures ranging from about 17 C to 21 C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial typically grown as a container and garden plant; relatively compact, upright to somewhat outwardly spreading plant habit; vigorous growth habit and rapid growth rate.

*Branching habit.*—Freely basal branching with about four to five primary lateral branches with secondary lateral branches potentially developing at every node; bushy and dense appearance.

*Plant height, soil level to top of foliar plane.*—About 15 cm.

*Plant height, soil level to top of floral plane.*—About 30 cm.

*Plant width.*—About 31 cm.

*Lateral branch description.*—Length: About 13 cm. Diameter: About 5 mm. Internode length: About 3.2 cm. Strength: Strong and sturdy. Aspect: Mostly upright to about 30 to 45 degrees from vertical. Texture and luster: Moderately pubescent, longitudinally ridged; matte. Color, developing: Close to N187A and 187A. Color, developed: Close to 146A variably tinged with closer to N187A and 187A.

Leaf description:

*Arrangement.*—Opposite, simple.

*Length.*—About 8.5 cm.

*Width.*—About 6.75 cm.

*Shape.*—Ovate.

*Apex.*—Acuminate.

*Base.*—Cordate to truncate.

*Margin.*—Crenate to serrate with shallow indentations.

*Texture and luster, upper surface.*—Sparsely pubescent, slightly rough; slightly glossy.

*Texture and luster, lower surface.*—Sparsely pubescent, slightly rough; matte.

*Venation pattern.*—Pinnate, reticulate.

*Fragrance.*—Pungent; not unpleasant.

*Color*.—Developing leaves, upper surface: More green than 146A. Developing leaves, lower surface: Close to 146A. Fully expanded leaves, upper surface: Darker green than 147A; venation, close to 146A. Fully expanded leaves, lower surface: Close to 147B; venation, close to 146A to 146B.

*Petioles*.—Length: About 6 cm. Diameter: About 4 mm. Strength: Moderately strong; flexible. Texture and luster, upper and lower surfaces: Moderately pubescent; slightly glossy. Color, upper surface: Close to between 144A and 146A. Color, lower surface: Close to 144A.

Flower description:

*Flower arrangement and shape*.—Single bilabiate flowers arranged on terminal and axillary racemes; freely flowering habit with about 24 to 36 flowers developing per inflorescence and more than 500 flowers developing per plant; flowers face mostly outwardly.

*Fragrance*.—None detected.

*Natural flowering season*.—Early flowering habit, plants begin flowering about seven weeks after planting; plants flower from late spring until frost in Michigan.

*Flower longevity*.—Flowers last about four to five days on the plant; flowers not persistent.

*Flower buds*.—Length: About 1.4 cm. Diameter: About 7 mm. Shape: Roughly clavate to elongated rhomboidal. Texture and luster: Slightly pubescence, velvety; matte. Color: Close to N92A.

*Inflorescence height*.—About 18.5 cm.

*Inflorescence diameter*.—About 10 cm.

*Flower height*.—About 1.75 cm.

*Flower diameter*.—About 7.5 mm.

*Flower length (depth)*.—About 4 cm.

*Flower throat diameter*.—About 4.5 mm.

*Flower tube length*.—About 2.5 cm.

*Flower tube diameter, proximally*.—About 3 mm.

*Petals*.—Arrangement: Five petals with two upper petals fused forming a galea and three lower petals fused forming a broader lower protruding lip. Upper galea length: About 1.5 cm. Upper galea width: About 4.5 mm. Lower lip length: About 1 cm. Lower lip width: About 8 mm. Shape: Upper galea, hood-like; lower lip, oblong, revolute and recurved. Upper galea apex: Round, obtuse. Lower lip apex: Round, obtuse. Base: Fused. Margin: Entire; not undulate. Upper galea, texture and luster, upper surface: Densely pubescent; matte. Upper galea, texture and luster, lower surface: Smooth, glabrous; matte. Lower lip, texture and luster, upper and lower surfaces: Smooth, glabrous, velvety; matte. Throat, texture and luster: Smooth, glabrous; slightly glossy. Tube, texture and luster: Sparsely pubescent; moderately glossy. Color, upper galea: When opening and fully opened, upper surface: Close to 83A; venation, close to 83A; color does not change with subsequent development. When opening and fully opened, lower surface: Close to 83A; venation, close to 83A; color does not change with subsequent development. Color, lower lip: When opening and fully opened, upper surface: Close to 83A; venation, close to 83A; color does not change with subsequent development. When opening and fully opened, lower surface: Close to 83A; venation, close to 83A; color does not change with subsequent development. Color, throat: Close to 83A and 83C; proximally, close to NN155D; venation, close to between 83A and 83C. Color, tube: Close to 83A; proximally, close to NN155D; venation, close to 83A.

*Calyx*.—Arrangement: Two sepals fused to form a tubular bilabiate calyx. Sepal length: About 2 cm. Sepal width: About 1 cm. Sepal shape: Elongated rhomboidal. Sepal apex: Cuspidate to mucronate. Sepal margin: Entire. Sepal texture and luster, inner and outer surfaces: Smooth, glabrous; matte. Color: When developing and fully developed, inner surface: Close to 144A variably tinged with close to N92A. When developing and fully developed, outer surface: Close to N92A.

*Peduncles*.—Length: About 18.5 cm. Diameter: About 2.5 mm. Strength: Strong. Aspect: Mostly erect. Texture and luster: Pubescent; matte. Color: Close to 148A variably tinged with close to 187A and N187A.

*Pedicels*.—Length: About 5 mm. Diameter: About 1 mm. Strength: Strong, flexible. Aspect: About 45 degrees from peduncle axis. Texture and luster: Moderately to densely pubescent; matte. Color: Close to 187A and N187A.

*Reproductive organs*.—Stamens: Quantity per flower: Two. Filament length: About 1.6 cm. Filament color: Distally, close to N82A and proximally, close to 83A. Anther size: About 4 mm by 1 mm. Anther shape: Oblong. Anther color: Close to 93A. Pollen amount: Scarce. Pollen color: Close to 2D. Pistils: Quantity per flower: One. Pistil length: About 4.1 cm. Stigma diameter: Less than 1 mm. Stigma shape: Bipartite. Stigma color: Close to 83A. Style length: About 3.9 cm. Style color: Distally, close to 83A and proximally, close to NN155D. Ovary color: Close to 154D.

*Seeds and fruits*.—To date, seed and fruit production has not been observed on plants of the new *Salvia* plant.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind and temperatures from about 2 C to 35 C.

It is claimed:

1. A new and distinct *Salvia* plant named 'WNSVRDP23' as illustrated and described.

* * * * *